United States Patent [19]

Noguchi et al.

[11] Patent Number: 4,666,943
[45] Date of Patent: May 19, 1987

[54] FUNGICIDAL ANILIDES

[75] Inventors: Hiroshi Noguchi, Toyonaka; Toshiro Kato, Takarazuka; Junya Takahashi, Nishinomiya; Yukio Ishiguri, Toyonaka; Shigeo Yamamoto, Ikeda; Naonori Hirata, Sakai, all of Japan

[73] Assignee: Sumitomo Chemical Company, Limited, Osaka, Japan

[21] Appl. No.: 514,799

[22] Filed: Jul. 19, 1983

[30] Foreign Application Priority Data

Jul. 27, 1982 [GB] United Kingdom ............... 8221706

[51] Int. Cl.⁴ .......................................... A01N 37/18
[52] U.S. Cl. ........................... 514/627; 514/625; 514/629; 564/223
[58] Field of Search .............. 564/223; 424/324; 514/625, 627, 629

[56] References Cited

U.S. PATENT DOCUMENTS

| | | | |
|---|---|---|---|
| 2,688,637 | 9/1954 | Coleman et al. | 424/324 |
| 3,108,038 | 10/1963 | Fielding et al. | 424/324 |
| 3,119,736 | 1/1964 | Clark et al. | 564/223 |
| 3,142,703 | 7/1964 | Stecker | 424/324 |
| 3,149,032 | 9/1964 | Waring | 424/324 |
| 3,492,349 | 1/1970 | Doyle et al. | 424/324 |
| 3,642,895 | 2/1972 | Adams, Jr. et al. | 424/324 |
| 3,966,809 | 6/1976 | Baker et al. | 424/324 |

FOREIGN PATENT DOCUMENTS

| | | | |
|---|---|---|---|
| 749581 | 10/1970 | Bulgaria | 424/324 |
| 915705 | 11/1972 | Canada | 564/223 |
| 1219947 | 6/1966 | Fed. Rep. of Germany | 564/223 |
| 44-29476 | 12/1969 | Japan | 424/324 |
| 46-30716 | 9/1971 | Japan | 424/324 |

OTHER PUBLICATIONS

"Chemical Abstracts" 49, 10233f (1955).
"Chemical Abstracts" 54, 8731h (1960).
"Chemical Abstracts" 84, 164487z (1976).
"Chemical Abstracts" 88, 89336b (1978).
"Chemical Abstracts" 88, 120763q (1978).

Primary Examiner—Allen J. Robinson
Attorney, Agent, or Firm—Birch, Stewart, Kolasch & Birch

[57] ABSTRACT

Use of an anilide of the formula:

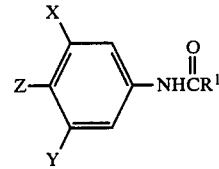

as a fungicidal agent against phytophatogenic fungi, particularly their strains resistant to benzimidazole thiophanate fungicides and/or cyclic imide fungicides.

13 Claims, No Drawings

FUNGICIDAL ANILIDES

This invention relates to fungicidal anilides.

Benzimidazole and thiophanate fungicides such as Benomyl (methyl 1-(butylcarbamoyl)benzimidazol-2yl-carbamate), Fubelidazol (2-(2-furyl)benzimidazole), Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)-benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene exhibit an excellent fungicidal activity against various plant pathogenic fungi, and they have been widely used as agricultural fungicides since 1970. However, their continuous application over a long period of time allows phytopathogenic fungi to develop a tolerance to them, whereby their plant disease-preventive effect is significantly decreased. Further, the fungi which developed tolerance to certain kinds of benzimidazole or thiophanate fungicides also exhibit considerable tolerance to some other kinds of benzimidazole or thiophanate fungicides. Thus, they are apt to develop cross-tolerance. Therefore, if any material decrease of their plant disease-preventive effect in certain fields is observed, their application to such fields has to be discontinued. But, it is often observed that the density of drug-resistant organisms is not reduced even long after the discontinuation of the application. Although other kinds of fungicides have to be employed in such a case, only few are so effective as benzimidazole or thiophanate fungicides in controlling various phytopathogenic fungi. Benzimidazole and thiophanate fungicides are hereinafter referred to as "benzimidazole thiophanate fungicides". Cyclic imide fungicides such as Procymidone (3-(3', 5'-dichlorophenyl)-1,2-dimethylcyclopropane-1,2-dicarboximide), Iprodione (3-(3', 5'-dichlorophenyl)-1-isopropylcarbamoylimidazolidine-2,4-dione), Vinchlozolin (3-(3', 5'-(dichlorophenyl)-5-methyl-5-vinyloxazolidine-2,4-dione), ethyl (RS)-3-(3', 5'-dichlorophenyl)-5-methyl-2,4-dioxooxazolidine-5-carboxylate, etc., which are effective against various plant diseases, particularly those caused by *Botrytis cinerea*, have the same defects as previously explained with respect to the benzimidazole thiophanate fungicides.

As a result of study seeking a new type of fungicides, it has now been found that anilides of the formula:

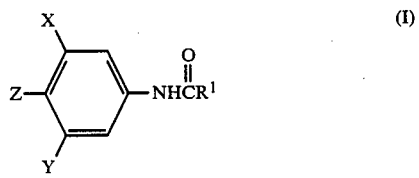

wherein X and Y are, same or different, each a halogen atom, a lower alkyl group, a lower alkenyl group, a lower cyanoalkenyl group, a lower alkynyl group, a lower alkoxy group, a cyano group, a lower alkyl group substituted with at least one member selected from the group consisting of halogen, hydroxyl and cyano, or a group of the formula:

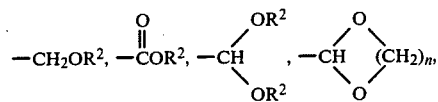

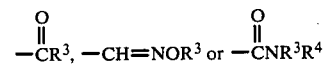

in which $R_2$ is a lower alkyl group, a lower alkenyl group, a lower alkynyl group or a lower haloalkyl group, $R_3$ and $R_4$ are, same or different, each a hydrogen atom or a lower alkyl group and n is 2, 3 or 4; Z is a hydrogen atom, a fluorine atom or a group of the formula: $OR_5$ in which $R_5$ is a lower alkyl group, a lower alkenyl group, a lower alkynyl group or a lower alkyl group substituted with at least one member selected from the group consisting of halogen, lower alkoxy and lower cycloalkyl; and $R_1$ is a $C_1$–$C_7$ alkyl group, a $C_2$–$C_6$ alkenyl group, a $C_2$–$C_6$ alkynyl group, a $C_3$–$C_7$ cycloalkyl group, a $C_1$–$C_6$ haloalkyl group, a lower haloalkenyl group, a lower alkyl group substituted with at least one member selected from the group consisting of cyano, lower alkoxy, lower cycloalkyl and phenoxy (phenoxy being optionally substituted with at least one halogen and/or at least one alkyl), a phenyl group, a phenyl group substituted with at least one member selected from the group consisting of halogen, cyano, nitro, trifluoromethyl, lower alkyl and lower alkoxy or an aralkyl group (aralkyl being optionally substituted with at least one halogen and/or at least one alkyl) exhibit an excellent fungicidal activity against plant pathogenic fungi which have developed resistance to benzimidazole thiophanate fungicides and/or cyclic imide fungicides. It is notable that their fungicidal potency against the organisms tolerant to benzimidazole thiophanate fungicides and/or cyclic imide fungicides (hereinafter referred to as "drug-resistant fungi" or "drug-resistant strains") is much higher than that against the organisms sensitive to benzimidazol thiophanate fungicides and/or cyclic imide fungicides (hereinafter referred to as "drug-sensitive fungi" or "drug-sensitive strains").

The term "lower" used hereinabove and hereinafter in connection with organic radicals or compounds indicates that such radicals or compounds each have not more than 4 carbon atoms. The term "halogen" used hereinabove and hereinafter indicates fluorine, chlorine, bromins or iodine.

Typical examples of the anilides of the formula (I) are shown in Table 1.

TABLE 1

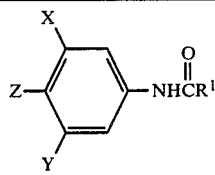

| X | Y | Z | R¹ |
|---|---|---|---|
| —CH₃ | —CH₃ | —H |  |
| —C₂H₅ | —C₂H₅ | —H | —CH=CHCH₃ |
| —OCH₃ | —OCH₃ | —H |  |
| —Cl | —Cl | —F | —C₃H₇(iso) |
| —CH₃ | —CH₃ | —OCH₃ | —C₃H₇(n) |
| —Cl | —Cl | —OC₂H₅ |  |
| —Cl | —Cl | —OCH₂CF₃ |  |
| —CH₃ | —CH₃ | —OC₂H₅ | —CH₃ |
| —CH₃ | —CH₃ | —OC₂H₅ | —C₂H₅ |
| —CH₃ | —CH₃ | —OC₂H₅ | —C₃H₇(n) |
| —CH₃ | —CH₃ | —OC₂H₅ | —C₃H₇(iso) |
| —CH₃ | —CH₃ | —OC₂H₅ | —CH=CH₂ |
| —CH₃ | —CH₃ | —OC₂H₅ |  |
| —CH₃ | —CH₃ | —OC₂H₅ | —CH=CHCH₃ |
| —CH₃ | —CH₃ | —OC₂H₅ |  |
| —CH₃ | —CH₃ | —OC₂H₅ | 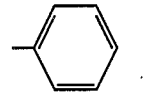 |
| —Cl | —OCH₃ | —OC₂H₅ | —C₃H₇(n) |
| —Cl | —OC₂H₅ | —OC₂H₅ | —CH₃ |
| —Cl | —OC₂H₅ | —OC₂H₅ | —C₂H₅ |
| —Cl | —OC₂H₅ | —OC₂H₅ | —C₃H₇(n) |
| —Cl | —OC₂H₅ | —OC₂H₅ | —C₃H₇(iso) |
| —Cl | —OC₂H₅ | —OC₂H₅ | —C₄H₉(n) |
| —Cl | —OC₂H₅ | —OC₂H₅ | —C₄H₉(sec) |
| —Cl | —OC₂H₅ | —OC₂H₅ | —C₄H₉(iso) |
| —Cl | —OC₂H₅ | —OC₂H₅ | —CH=CH₂ |
| —Cl | —OC₂H₅ | —OC₂H₅ |  |
| —Cl | —OC₂H₅ | —OC₂H₅ | —CH=CHCH₃ |

TABLE 1-continued $$\underset{Y}{\overset{X}{\underset{Z}{\bigoplus}}}-NH\overset{O}{\underset{}{C}}R^1$$

| X | Y | Z | R¹ |
|---|---|---|---|
| —Cl | —OC$_2$H$_5$ | —OC$_2$H$_5$ | cyclopropyl |
| —Cl | —OC$_2$H$_5$ | —OC$_2$H$_5$ | cyclopentyl-H |
| —Cl | —OC$_2$H$_5$ | —OC$_2$H$_5$ | —CH$_2$OCH$_3$ |
| —Cl | —OC$_2$H$_5$ | —OC$_3$H$_7$(n) | —C$_2$H$_5$ |
| —Cl | —OC$_2$H$_5$ | —OCH$_2$CH=CH$_2$ | —C$_3$H$_7$(iso) |
| —Cl | —OC$_2$H$_5$ | —OCH$_2$cyclopropyl | —CH=CHCH$_3$ |
| —Cl | —OC$_2$H$_5$ | —OCH$_2$CH$_2$OCH$_3$ | cyclopropyl |
| —Cl | —OC$_2$H$_5$ | —OCH$_2$CH$_2$Cl | —C$_3$H$_7$(n) |
| —Cl | —OC$_2$H$_5$ | —OCH$_2$C≡CH | cyclopropyl |
| —Br | —OCH$_3$ | —OC$_2$H$_5$ | 3-chlorophenyl |
| —CH$_3$ | —OCH$_3$ | —OC$_2$H$_5$ | —C$_3$H$_7$(iso) |
| —CH$_3$ | —OC$_2$H$_5$ | —OC$_2$H$_5$ | —CH$_3$ |
| —CH$_3$ | —OC$_2$H$_5$ | —OC$_2$H$_5$ | —C$_2$H$_5$ |
| —CH$_3$ | —OC$_2$H$_5$ | —OC$_2$H$_5$ | —C$_3$H$_7$(n) |
| —CH$_3$ | —OC$_2$H$_5$ | —OC$_2$H$_5$ | —C$_3$H$_7$(iso) |
| —CH$_3$ | —OC$_2$H$_5$ | —OC$_2$H$_5$ | —C$_4$H$_9$(sec) |
| —CH$_3$ | —OC$_2$H$_5$ | —OC$_2$H$_5$ | —C$_4$H$_9$(iso) |
| —CH$_3$ | —OC$_2$H$_5$ | —OC$_2$H$_5$ | —C$_4$H$_9$(tert) |
| —CH$_3$ | —OC$_2$H$_5$ | —OC$_2$H$_5$ | —CH=CH$_2$ |
| —CH$_3$ | —OC$_2$H$_5$ | —OC$_2$H$_5$ | —C(CH$_3$)=CH$_2$ |
| —CH$_3$ | —OC$_2$H$_5$ | —OC$_2$H$_5$ | —CH=CHCH$_3$ |
| —CH$_3$ | —OC$_2$H$_5$ | —OC$_2$H$_5$ | —CH=C(CH$_3$)$_2$ |
| —CH$_3$ | —OC$_2$H$_5$ | —OC$_2$H$_5$ | cyclopropyl |

TABLE 1-continued

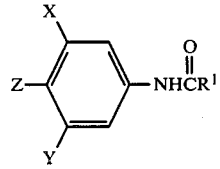

| X | Y | Z | R¹ |
|---|---|---|---|
| —CH₃ | —OC₂H₅ | —OC₂H₅ | 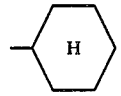 |
| —CH₃ | —OC₂H₅ | —OC₂H₅ | —CH₂Cl |
| —CH₃ | —OC₂H₅ | —OC₂H₅ | —CH₂OCH₃ |
| —CH₂CH=CH₂ | —CH₃ | —OC₂H₅ | —C₃H₇(n) |
| —C≡CH | —OC₂H₅ | —OC₂H₅ | —C₃H₇(n) |
| —CHCH₂Br<br>\|<br>Br | —OC₂H₅ | —OC₂H₅ |  |
| —CN | —OC₂H₅ | —OC₂H₅ | —C₃H₇(iso) |
| —OCH₃ | —OC₂H₅ | —OC₂H₅ | —CH=CHCH₃ |
| —COOCH₃ | —OC₂H₅ | —OC₂H₅ | —C₃H₇(n) |
| —COCH₃ | —OC₂H₅ | —OC₂H₅ | —C₂H₅ |
| —CHO | —OC₂H₅ | —OC₂H₅ | —C₃H₇(iso) |
| —CH(OCH₃)₂ | —OC₂H₅ | —OC₂H₅ | —C₃H₇(iso) |
| —CH=NOCH₃ | —OC₂H₅ | —OC₂H₅ | —C₃H₇(iso) |
| —CH₂OCH₃ | —OC₂H₅ | —OC₂H₅ | 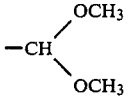 |
| —CONHCH₃ | —OC₂H₅ | —OC₂H₅ |  |
| —Cl | —CH₂OCH₃ | —OC₂H₅ | —CH₃ |
| —Cl | —CH₂OCH₃ | —OC₂H₅ | —C₂H₅ |
| —Cl | —CH₂OCH₃ | —OC₂H₅ | —C₃H₇(n) |
| —Cl | —CH₂OCH₃ | —OC₂H₅ | —C₃H₇(iso) |
| —Cl | —CH₂OCH₃ | —OC₂H₅ | —CH=CHCH₃ |
| —Cl | —CH₂OCH₃ | —OC₂H₅ |  |
| —Cl | —CH₂OCH₃ | —OC₂H₅ | —CH₂CH₂Cl |
| —Cl | —CH₂OCH₃ | —OC₂H₅ | —CH₂CN |
| —Cl | —CH₂OCH₃ | —OC₂H₅ |  |
| —Cl | —CH₂OCH₃ | —OC₂H₅ | 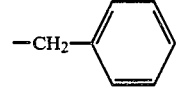 |
| —CH₃ | —CH₂OCH₃ | —OC₂H₅ | —C₂H₅ |
| —CH₃ | —CH₂OCH₃ | —OC₂H₅ | —C₃H₇(n) |

TABLE 1-continued

[Structure: benzene ring with X' (top), Z (left), Y (bottom), and NHC(=O)R¹ (right) substituents]

| X | Y | Z | R¹ |
|---|---|---|---|
| —CH₃ | —CH₂OCH₃ | —OC₂H₅ | —C₃H₇(iso) |
| —CH₃ | —CH₂OCH₃ | —OC₂H₅ | —CH=CHCH₃ |
| —CH₃ | —CH₂OCH₃ | —OC₂H₅ |  (cyclopropyl) |
| —Cl | —Cl | —H |  (cyclopropyl) |
| —CH₃ | —OC₂H₅ | —OC₂H₅ | —CH(C₂H₅)(CH₂)₃CH₃ |
| —CH₃ | —OC₂H₅ | —OC₂H₅ | —C₅H₁₁(n) |
| —CH₃ | —OC₂H₅ | —OC₂H₅ | —CH(C₂H₅)C₂H₅ |
| —CH₃ | —OC₂H₅ | —OC₂H₅ | 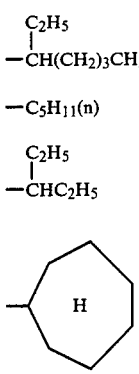 (cycloheptyl) |
| —CH₃ | —CH₃ | —OC₂H₅ |  (cyclobutyl) |
| —CH₃ | —OC₂H₅ | —OC₂H₅ | 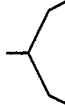 (cyclobutyl) |
| —Cl | —CH₂OCH₃ | —OC₂H₅ |  (cyclobutyl) |
| —CH₃ | —OC₂H₅ | —OC₂H₅ |  (cyclopentyl) |
| —Cl | —CH₂OCH₃ | —OC₂H₅ |  (cyclopentyl) |
| —CH₂CH=CH₂ | —CH₃ | —OC₂H₅ | —C₃H₇(iso) |
| —Cl | —OC₂H₅ | —OCH₂CH₂Cl |  (cyclopropyl) |

TABLE 1-continued

| X | Y | Z | R¹ |
|---|---|---|---|
| —Cl | —CH₃ | —OC₂H₅ | 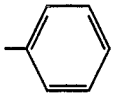 (cyclopropyl) |
| —Cl | —OC₂H₅ | —OCH₂CH=CH₂ | —C₂H₅ |
| —Cl | —Cl | —OCHF₂ | 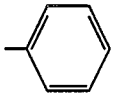 (phenyl) |
| —Cl | —Cl | —F | —C₂H₅ |
| —Cl | —CH₂OCH₃ | —OC₂H₅ | —CH₂Cl |
| —C₃H₇(n) | —OCH₃ | —OC₂H₅ | —C₃H₇(iso) |
| —Cl | —CH₂OCH₃ | —OCH₂C≡CH | 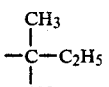 (phenyl) |
| —COC₂H₅ | —CH₃ | —OC₂H₅ | —CH=CHCH₃ |
| —CH=CHCH₃ | —OCH₃ | —OC₂H₅ | —C₃H₇(iso) |
| —Cl | —Cl | —OC₂H₅ | $-\underset{\underset{CN}{\vert}}{\overset{\overset{CH_3}{\vert}}{C}}-C_2H_5$ |
| —CH₃ | —CH₃ | —OC₂H₅ | $-\underset{\underset{CN}{\vert}}{CH}CH(CH_3)_2$ |

Some of the anilides (I) have hitherto been synthesized; for instance, N-(3-bromo-4,5-dimethoxyphenyl)acetamide (C.A., 49, 10234a), N-(3-acetyl-4-allyloxy-5-propylphenyl)acetamide (C.A., 54, 8732d), N-(3,5-dichloro-4-methoxyphenyl)-2-bromoacetamide (C.A., 84, 164487z), N-(3,5-dichloro-4-ethoxyphenyl)-2-methylpropanamide (ibid.) and so on are known. Several of them have been known to exhibit antipyretic or herbicidal activity. However, it has not been known or reported that they have fungicidal activity or are useful as fungicides.

Thus, the present invention provides a fungicidal composition which comprises, as an active ingredient, a fungicidally effective amount of the anilide of the formula (I) and an inert carrier or diluent. It also provides a combination composition comprising as active ingredients the anilide of the formula (I) together with a benzimidazole thiophanate fungicide and/or a cyclic imide fungicide, which is fungicidally effective against not only drug-sensitive fungi but also drug-resistant fungi, and hence particularly effective for the prevention of plant diseases. It also provides a method of controlling plant pathogenic fungi including drug-resistant strains and drug-sensitive strains by applying a fungicidally effective amount of the anilide of the formula (I) to plant pathogenic fungi.

Further, it provides nove anilides which are representable by the formula:

wherein X and Y are, same or different, each a halogen atom, a lower alkyl group, a lower alkenyl group, a lower cyanoalkenyl group, a lower alkynyl group, a lower alkoxy group, a cyano group, a lower alky group substituted with at least one member selected from the group consisting of halogen, hydroxyl and cyano, or a group of the formula:

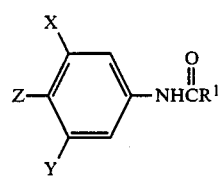

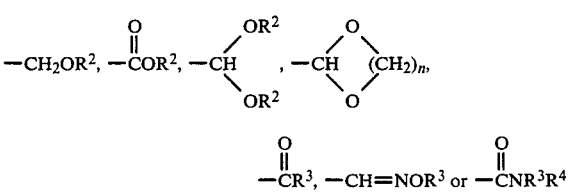

in which $R_2$ is a lower alkyl group, a lower alkenyl group, a lower alkynyl group or a lower haloalkyl group, $R_3$ and $R_4$ are, same or different, each a hydrogen atom or a lower alkyl group and n is 2, 3 or 4; Z is a fluoride atom or a group of the formula: $OR_5$ in which $R_5$ is a lower alkyl group, a lower alkenyl group, a lower alkynyl group or a lower alkyl group substituted with at least one member selected from the group consisting of halogen, lower alkoxy and lower cycloalkyl; and $R_1$ is a $C_2$–$C_7$ alkyl group, a $C_2$–$C_6$ alkenyl group, a $C_2$–$C_6$ alkynyl group, a $C_3$–$C_7$ cycloalkyl group, a $C_2$–$C_6$ haloalkyl group, a lower haloalkenyl group, a lower alkyl group substituted with at least one member selected from the group consisting of cyano, lower alkoxy, lower cycloalkyl and phenoxy (phenoxy being optionally substituted with at least one halogen and/or at least one alkyl), a phenyl group, a phenyl group substituted with at least one member selected from the group consisting of halogen, cyano, nitro, trifluoromethyl, lower alkyl and lower alkoxy or an aralkyl group (aralkyl being optionally substituted with at least one halogen and/or at least one alkyl), with the provisos that when X and Y are same and represent chlorine or bromine, Z is neither methoxy nor ethoxy, that X, Y and Z are not simultaneously methoxy, and that when X and Y are same and represent chlorine and Z is fluorine, $R_1$ is neither isopropyl nor isopropenyl. It furthermore provides a process for producing the novel anilides.

Accccording to the present invention, the anilides (I) can be prepared by reacting a 3,4,5-trisubstituted aniline of the formula:

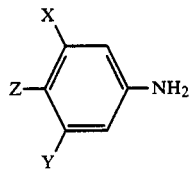

(II)

wherein X, Y and Z are each as defined above, with a carboxylic acid of the formula:

(III)

wherein $R_1$ is as defined above or its reactiv derivative at the carboxyl group such as a carboxylic acid halide of the formula:

(IV)

wherein $R_1$ is as defined above and B is a halogen atom or a carboxylic acid anhydride of the formula:

(V)

wherein $R_1$ is as defined above.

The starting 3,4,5-trisubstituted aniline (II) can be produced by a known procedure (cf. EP-A-0063905) or any analogous procedure thereto.

The anilides (I) are fungicidally effective against a wide scope of plant pathogenic fungi, of which examples are as follows: *Podosphaera leucotricha, Venturia inaequalis, Mycosphaerella pomi, Marssonina mali* and *Sclerotinia mali* of apple, *Phyllactinia kakicola* and *Gloeosporium kaki* of persimmon, *Cladosporium carpophilum* and *Phomopsis* sp. of peach, *Cercospora viticola, Uncinula necator, Elsinoe ampelina* and *Glomerella cingulata* of grape, *Cercospora beticola* of sugarbeet, *Cercospora arachidicola* and *Cercospora personata* of peanut, *Erysiphe graminis* f. sp. *hordei, Cercosporella herpotrichoides* and *Fusarium nivale* of barley, *Erysiphe graminis* f. sp. *tritici* of wheat, *Sphaerotheca fuliginea* and *Cledosporium cucumerinum* of cucumber, *Cladosporium fulvum* of tomato, *Corynespora melogenae* of eggplant, *Sphaerotheca humuli, Fusarium oxysporum* f. sp. *fragariae* of strawberry, *Botrytis alli* of onion, *Cercospora apii* of cerely, *Phaeoisariopsis griseola* of kidney bean, *erysiphe cichoracearum* of tobacco, *Diplocarpon rosae* of rose, *Elsinoe fawcetti, Penicillium italicum, Penicillium digitatum* of orange, *Botrytis cinerea* of cucumber, eggplant, tomato, strawberry, pimiento, onion, lettuce, grape, orange, cyclamen, rose or hop, *Sclerotinia sclerotiorum* of cucumber, eggplant, pimiento, lettuce, celery, kidney bean, soybean, azuki bean, potato or sunflower, *Sclerotinia cinerea* of peach or cherry, *Mycosphaerella melonis* of cucumber or melon, etc. Namely, the anilides (I) are highly effective in controlling the drug-resistant strains of the fungi.

The anilides (I) are also fungicidally effective against fungi to which known fungicides are ineffective. Examples of such fungi are *Pyricularia oryzae, Pseudoperonospora cubensis, Plasmopara viticola, Phytophthora infestans*, etc.

Advantageously, the anilides (I) are low in toxicity and have little detrimental effects on mammals and so on. Also, they may be applied to an agricultural field without causing any material toxicity to important crop plants.

Typical examples of the procedure for preparation of the anilides (I) are shown in the following examples.

EXAMPLE 1

Preparation of N-(3,5-dimethyl-4-ethoxyphenyl)-2-butenamide

To a solution of 2-butenoic acid (0.86 g) in tetrahydrofuran (30 ml), 3,5-dimethyl-4-ethoxyaninline (1.65 g) was added, and a solution of N,N'-dicyclohexylcarbodiimide (D.C.C.) (2.2 g) in tetrahydrofuran (20 ml) was dropwise added threto while stirring. After 30 minutes, the by-produced N,N'-dicyclohexylurea (D.C.U.) was removed by filtration. To the filtrate was added acetic acid (2 ml) to decompose excessive D.C.C., followed by filtration of D.C.U. The resultant filtrate was poured into ice-water and extracted with ether. The extract was washed with 1N hydrochloric acid, sodium bicarbonate solution and saturated brine, dried over anhydrous magnesium sulfate and concentrated under reduced pressure. The residue was purified by silica gel chromatography using hexane-acetone as the eluent to give N-(3,5-dimethyl-4-ethoxyphenyl)-2butenamide (Compound No. 12) (2.17 g) in a yield of 93%. M.P., 118°–119° C.

EXAMPLE 2

Preparation of N-(3,4-diethoxy-5-methylphenyl)cyclopropanecarboxamide 3,4-Diethoxy-5-methylaniline (1.95 g) and triethylamine (1.01 g) were dissolved in toluene (20 ml). To the rsultant solution was dropwise added cyclopropanecarboxylic acid chloride (1.05 g) in 10 minutes under ice-cooling. After being stirred at room temperature for 5 hours, the reaction mixture was poured into ice water and extracted with toluene. The extract was washed with 1N hydrochloric acid, sodium bicarbonate solution and saturated brine, dried over anhydrous magnesium sulfate and concentrated under reduced pressure to give crude crystals (2.55 g). Recrystallization from ethanol gave N-(3,4-diethoxy)-5-methylphenyl)cyclopropanecarboxamide (Compound No. 44) (2.32 g) in a yield of 88%. M.P., 120°–121° C.

In the same manner as above, the anilides of the formula (I) as shown in Table 2 can be prepared:

TABLE 2

[Structure: benzene ring with X at top, Z on left, Y at bottom, and —NHC(=O)R¹ on right]

| Compound No. | X | Y | Z | R¹ | Physical constant |
| --- | --- | --- | --- | --- | --- |
| 1 | —CH₃ | —CH₃ | —H | cyclopropyl | M.P. 123–124° C. |
| 2 | —OCH₃ | —OCH₃ | —H | cyclopropyl | M.P. 114–115° C. |
| 3 | —Cl | —Cl | —F | —C₃H₇(iso) | M.P. 195–196° C. |
| 4 | —Cl | —Cl | —OC₂H₅ | cyclopropyl | M.P. 153–155° C. |
| 5 | —Cl | —Cl | —OCH₂CF₃ | cyclopropyl | M.P. 155–156° C. |
| 6 | —CH₃ | —CH₃ | —OC₂H₅ | —CH₃ | M.P. 132–133° C. |
| 7 | —CH₃ | —CH₃ | —OC₂H₅ | —C₂H₅ | M.P. 99–100° C. |
| 8 | —CH₃ | —CH₃ | —OC₂H₅ | —C₃H₇(n) | M.P. 78–79° C. |
| 9 | —CH₃ | —CH₃ | —OC₂H₅ | —C₃H₇(iso) | M.P. 121–122° C. |
| 10 | —CH₃ | —CH₃ | —OC₂H₅ | —CH=CH₂ | M.P. 82–83.5° C. |
| 11 | —CH₃ | —CH₃ | —OC₂H₅ | —C(CH₃)=CH₂ | M.P. 75–76° C. |
| 12 | —CH₃ | —CH₃ | —OC₂H₅ | —CH=CHCH₃ | M.P. 118–119° C. |
| 13 | —CH₃ | —CH₃ | —OC₂H₅ | cyclopropyl | M.P. 148–149° C. |
| 14 | —CH₃ | —CH₃ | —OC₂H₅ | phenyl | M.P. 153–154° C. |
| 15 | —Cl | —OCH₃ | —OC₂H₅ | —C₃H₇(n) | M.P. 81.5–83° C. |
| 16 | —Cl | —OC₂H₅ | —OC₂H₅ | —CH₃ | M.P. 106–107° C. |
| 17 | —Cl | —OC₂H₅ | —OC₂H₅ | —C₂H₅ | M.P. 101–102° C. |
| 18 | —Cl | —OC₂H₅ | —OC₂H₅ | —C₃H₇(n) | M.P. 80–81° C. |
| 19 | —Cl | —OC₂H₅ | —OC₂H₅ | —C₃H₇(iso) | $n_D^{26}$ 1.5241 |
| 20 | —Cl | —OC₂H₅ | —OC₂H₅ | —C₄H₉(n) | M.P. 66–67° C. |
| 21 | —Cl | —OC₂H₅ | —OC₂H₅ | —C₄H₉(sec) | M.P. 102–103° C. |
| 22 | —Cl | —OC₂H₅ | —OC₂H₅ | —C₄H₉(iso) | M.P. 91–92° C. |
| 23 | —Cl | —OC₂H₅ | —OC₂H₅ | —CH=CH₂ | M.P. 106–107° C. |
| 24 | —Cl | —OC₂H₅ | —OC₂H₅ | —C(CH₃)=CH₂ | $n_D^{24}$ 1.5452 |

TABLE 2-continued

| Compound No. | X | Y | Z | R¹ | Physical constant |
|---|---|---|---|---|---|
| 25 | —Cl | —OC$_2$H$_5$ | —OC$_2$H$_5$ | —CH=CHCH$_3$ | M.P. 95–96° C. |
| 26 | —Cl | —OC$_2$H$_5$ | —OC$_2$H$_5$ | cyclopropyl | M.P. 102–104° C. |
| 27 | —Cl | —OC$_2$H$_5$ | —OC$_2$H$_5$ | cyclopentyl | M.P. 80–81° C. |
| 28 | —Cl | —OC$_2$H$_5$ | —OC$_2$H$_5$ | —CH$_2$OCH$_3$ | wax |
| 29 | —Cl | —OC$_2$H$_5$ | —OC$_3$H$_7$(n) | —C$_2$H$_5$ | M.P. 95–96° C. |
| 30 | —Cl | —OC$_2$H$_5$ | —OCH$_2$CH=CH$_2$ | —C$_3$H$_7$(iso) | M.P. 50–53° C. |
| 31 | —Cl | —OC$_2$H$_5$ | —OCH$_2$CH$_2$Cl | —C$_3$H$_7$(n) | M.P. 84–86° C. |
| 32 | —Cl | —OC$_2$H$_5$ | —OCH$_2$C≡CH | cyclopropyl | M.P. 73–75° C. |
| 33 | —Br | —OCH$_3$ | —OC$_2$H$_5$ | 3-chlorophenyl | M.P. 119–120° C. |
| 34 | —CH$_3$ | —OC$_2$H$_5$ | —OC$_2$H$_5$ | —CH$_3$ | M.P. 87.5–89° C. |
| 35 | —CH$_3$ | —OC$_2$H$_5$ | —OC$_2$H$_5$ | —C$_2$H$_5$ | M.P. 89.5–91° C. |
| 36 | —CH$_3$ | —OC$_2$H$_5$ | —OC$_2$H$_5$ | —C$_2$H$_7$(n) | M.P. 44–46° C. |
| 37 | —CH$_3$ | —OC$_2$H$_5$ | —OC$_2$H$_5$ | —C$_3$H$_7$(iso) | M.P. 92–93° C. |
| 38 | —CH$_3$ | —OC$_2$H$_5$ | —OC$_2$H$_5$ | —C$_4$H$_9$(sec) | M.P. 91–92.5° C. |
| 39 | —CH$_3$ | —OC$_2$H$_5$ | —OC$_2$H$_5$ | —C$_4$H$_9$(tert) | M.P. 127–128° C. |
| 40 | —CH$_3$ | —OC$_2$H$_5$ | —OC$_2$H$_5$ | —CH=CH$_2$ | M.P. 82–83° C. |
| 41 | —CH$_3$ | —OC$_2$H$_5$ | —OC$_2$H$_5$ | —C(CH$_3$)=CH$_2$ | M.P. 51.5–53° C. |
| 42 | —CH$_3$ | —OC$_2$H$_5$ | —OC$_2$H$_5$ | —CH=CHCH$_3$ | M.P. 85–86.5° C. |
| 43 | —CH$_3$ | —OC$_2$H$_5$ | —OC$_2$H$_5$ | —CH=C(CH$_3$)$_2$ | M.P. 134–135° C. |
| 44 | —CH$_3$ | —OC$_2$H$_5$ | —OC$_2$H$_5$ | cyclopropyl | M.P. 120–121° C. |
| 45 | —CH$_3$ | —OC$_2$H$_5$ | —OC$_2$H$_5$ | cyclohexyl | M.P. 117–118° C. |
| 46 | —CH$_3$ | —OC$_2$H$_5$ | —OC$_2$H$_5$ | —CH$_2$Cl | M.P. 120–121° C. |
| 47 | —CH$_3$ | —OC$_2$H$_5$ | —OC$_2$H$_5$ | —CH$_2$OCH$_3$ | $n_D^{26}$ 1.5185 |
| 48 | —CH$_2$CH=CH$_2$ | —CH$_3$ | —OC$_2$H$_5$ | —C$_3$H$_7$(n) | $n_D^{24}$ 1.5302 |
| 49 | —C≡CH | —OC$_2$H$_5$ | —OC$_2$H$_5$ | —C$_3$H$_7$(n) | M.P. 83–84° C. |
| 50 | —COOCH$_3$ | —OC$_2$H$_5$ | —OC$_2$H$_5$ | —C$_3$H$_7$(n) | M.P. 67–68° C. |
| 51 | —CHO | —OC$_2$H$_5$ | —OC$_2$H$_5$ | —C$_3$H$_7$(iso) | M.P. 98.5–100° C. |
| 52 | —Cl | —CH$_2$OCH$_3$ | —OC$_2$H$_5$ | —CH$_3$ | M.P. 99–100° C. |

TABLE 2-continued

Structure:

X, Y, Z substituted on benzene ring with NHC(=O)R¹

| Compound No. | X | Y | Z | R¹ | Physical constant |
|---|---|---|---|---|---|
| 53 | —Cl | —CH₂OCH₃ | —OC₂H₅ | —C₂H₅ | M.P. 58–59° C. |
| 54 | —Cl | —CH₂OCH₃ | —OC₂H₅ | —C₃H₇(n) | $n_D^{23.5}$ 1.5346 |
| 55 | —Cl | —CH₂OCH₃ | —OC₂H₅ | —C₃H₇(iso) | M.P. 82–83° C. |
| 56 | —Cl | —CH₂OCH₃ | —OC₂H₅ | —CH=CHCH₃ | $n_D^{24}$ 1.5571 |
| 57 | —Cl | —CH₂OCH₃ | —OC₂H₅ | cyclopropyl | M.P. 109–110° C. |
| 58 | —Cl | —CH₂OCH₃ | —OC₂H₅ | —CH₂CH₂Cl | M.P. 81–82° C. |
| 59 | —Cl | —CH₂OCH₃ | —OC₂H₅ | —CH₂-phenyl | M.P. 110–111° C. |
| 60 | —Cl | —CH₂OCH₃ | —OC₂H₅ | —CH₂O-phenyl | M.P. 88–89° C. |
| 61 | —CH₃ | —CH₂OCH₃ | —OC₂H₅ | —C₂H₅ | M.P. 68–69° C. |
| 62 | —CH₃ | —CH₂OCH₃ | —OC₂H₅ | —C₃H₇(n) | $n_D^{25}$ 1.5171 |
| 63 | —CH₃ | —CH₂OCH₃ | —OC₂H₅ | —C₃H₇(iso) | M.P. 122–123° C. |
| 64 | —CH₃ | —CH₂OCH₃ | —OC₂H₅ | —CH=CHCH₃ | $n_D^{25}$ 1.5347 |
| 65 | —CH₃ | —CH₂OCH₃ | —OC₂H₅ | cyclopropyl | $n_D^{25}$ 1.5369 |
| 66 | —Cl | —Cl | —H | cyclopropyl | M.P. 169–170° C. |
| 67 | —CH₃ | —OC₂H₅ | —OC₂H₅ | —CH(C₂H₅)(CH₂)₃CH₃ | M.P. 108–109.5° C. |
| 68 | —CH₃ | —OC₂H₅ | —OC₂H₅ | —C₅H₁₁(n) | $n_D^{26}$ 1.5040 |
| 69 | —CH₃ | —OC₂H₅ | —OC₂H₅ | —CH(C₂H₅)C₂H₅ | M.P. 130–133° C. |
| 70 | —CH₃ | —OC₂H₅ | —OC₂H₅ | cycloheptyl | M.P. 136–137° C. |
| 71 | —CH₃ | —CH₃ | —OC₂H₅ | cyclobutyl | M.P. 108–109° C. |
| 72 | —CH₃ | —OC₂H₅ | —OC₂H₅ | cyclobutyl | M.P. 91–92.5° C. |

TABLE 2-continued

Structure: phenyl ring with X (top), Z (left), Y (bottom), and —NHC(=O)R¹ (right)

| Compound No. | X | Y | Z | R¹ | Physical constant |
|---|---|---|---|---|---|
| 73 | —Cl | —CH$_2$OCH$_3$ | —OC$_2$H$_5$ | cyclobutyl (H) | M.P. 96–97° C. |
| 74 | —CH$_3$ | —OC$_2$H$_5$ | —OC$_2$H$_5$ | cyclopentyl (H) | M.P. 92–93° C. |
| 75 | —Cl | —CH$_2$OCH$_3$ | —OC$_2$H$_5$ | cyclopentyl (H) | $n_D^{26}$ 1.5246 |
| 76 | —CH$_2$CH=CH$_3$ | —CH$_3$ | —OC$_2$H$_5$ | —C$_3$H$_7$(iso) | M.P. 85–86° C. |
| 77 | —Cl | —OC$_2$H$_5$ | —OCH$_2$CH$_2$Cl | cyclopropyl | M.P. 122–123° C. |
| 78 | —Cl | —CH$_3$ | —OC$_2$H$_5$ | cyclopropyl | M.P. 141.5–143° C. |
| 79 | —Cl | —OC$_2$H$_5$ | —OCH$_2$CH=CH$_2$ | —C$_2$H$_5$ | M.P. 83–84° C. |
| 80 | —Cl | —Cl | —OCHF$_2$ | phenyl | M.P. 140–141° C. |
| 81 | —Cl | —Cl | —F | —C$_2$H$_5$ | M.P. 132–133.5° C. |
| 82 | —Cl | —CH$_2$OCH$_3$ | —OC$_2$H$_5$ | —CH$_2$Cl | M.P. 49–51° C. |
| 83 | —C$_3$H$_7$(n) | —OCH$_3$ | —OC$_2$H$_5$ | —C$_3$H$_7$(iso) | M.P. 92–93.5° C. |
| 84 | —Cl | —CH$_2$OCH$_3$ | —OCH$_2$C≡CH | phenyl | $n_D^{24}$ 1.5952 |
| 85 | —COC$_2$H$_5$ | —CH$_3$ | —OC$_2$H$_5$ | —CH=CHCH$_3$ | $n_D^{27}$ 1.5591 |
| 86 | —CH=CHCH$_3$ | —OCH$_3$ | —OC$_2$H$_5$ | —C$_3$H$_7$(iso) | M.P. 97.5–98.5° C. |
| 87 | —Cl | —OC$_2$H$_5$ | —OCH$_2$CH$_2$OCH$_3$ | cyclopropyl | M.P. 78–81° C. |
| 88 | —CH$_3$ | —OC$_2$H$_5$ | —OC$_2$H$_5$ | —C$_4$H$_9$(iso) | wax |
| 89 | —CN | —OC$_2$H$_5$ | —OC$_2$H$_5$ | —C$_3$H$_7$(iso) | M.P. 101–102° C. |
| 90 | —Cl | —Cl | —OC$_2$H$_5$ | —C(CH$_3$)(C$_2$H$_5$)(CN) | M.P. 84–86° C. |

TABLE 2-continued $$\underset{Y}{\overset{X}{\underset{Z}{\bigoplus}}}-NHCR^1\overset{O}{\|}$$

| Compound No. | X | Y | Z | R$^1$ | Physical constant |
|---|---|---|---|---|---|
| 91 | —CH$_3$ | —CH$_3$ | —OC$_2$H$_5$ | —CH(CN)CH(CH$_3$)$_2$ | M.P. 121–123° C. |

In the practical use of the anilides (I) as fungicides, they may be applied as such or in a formulation form such as dusts, wettable powders, oil sprays, emulsifiable concentrates, tablets, granules, fine granules, aerosols or flowables. Such a formulation form can be formulated in a conventional manner by mixing at least one of the anilides (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw sust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride). Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include cesein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, various fatty acids and their esters, etc.

The foregoing formulations generally contain at least one of the anilides (I) in a concentration of about 1 to 95% by weight, preferably of 2.0 to 80% by weight. By using the formulations, the anilides (I) are generally applied in such amounts as 2 to 100 g per 10 are.

When only the drug-resistant strains of phytopathogenic fungi are present, the anilides (I) may be used alone. However, when the drug-sensitive strains are present together with the drug-resistant strains, their alternate use with benzimidazole thiophanate fungicides and/or cyclic imide fungicides or their combined use with benzimidazole thiophanate fungicides and/or cyclic imide fungicides is favorable. In such an alternate or combined use, each active ingredient may be employed as such or in conventional agricultural formulation forms. In case of the combined use, the weight proportion of the anilide (I) and the benzimidazole thiophanate fungicide and/or the cyclic imide fungicide may be from about 1:0.1 to 1:10.0.

Typical examples of the benzimidazole thiophanate fungicides and the cyclic imnide fungicides are shown in Table 3.

TABLE 3

| Compound | Structure | Name |
|---|---|---|
| A | 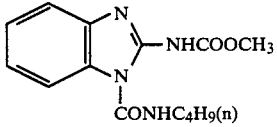 | Methyl 1-(butylcarbamoyl)benzimidazol-2-ylcarbamate |
| B | 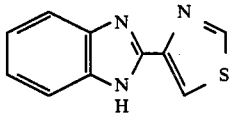 | 2-(4-Thiazolyl)benzimidazole |
| C | 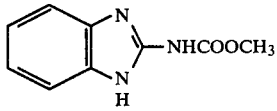 | Methyl benzimidazol-2-ylcarbamate |

TABLE 3-continued

| Compound | Structure | Name |
|---|---|---|
| D | benzimidazole with 2-furyl substituent | 2-(2-Furyl)benzimidazole |
| E | 1,2-C₆H₄(NHC(S)NHCOOCH₃)₂ | 1,2-Bis(3-methoxycarbonyl-2-thioureido)benzene |
| F | 1,2-C₆H₄(NHC(S)NHCOOC₂H₅)₂ | 1,2-Bis(3-ethoxycarbonyl-2-thioureido)benzene |
| G | benzene with NHC(S)NHCOOCH₃ and NHP(O)(SCH₃)(OCH₃) | 2-(O,S—Dimethylphosphorylamino)-1-(3'-methoxycarbonyl-2'-thioureido)benzene |
| H | benzene with NHC(S)NHCOOCH₃ and NHP(S)(OCH₃)₂ | 2-(O,O—Dimethylthiophosphorylamino)-1-(3'-methoxycarbonyl-2'-thioureido)benzene |
| I | N-(3,5-dichlorophenyl)-1,2-dimethylcyclopropane-1,2-dicarboximide structure | N—(3',5'-Dichlorophenyl)-1,2-dimethylcyclopropane-1,2-dicarboximide |
| J | 3-(3,5-dichlorophenyl)-1-isopropylcarbamoylimidazolidine-2,4-dione structure | 3-(3',5'-Dichlorophenyl)-1-isopropylcarbamoylimidazolidine-2,4-dione |
| K | 3-(3,5-dichlorophenyl)-5-methyl-5-vinyloxazolidine-2,4-dione structure | 3-(3',5'-Dichlorophenyl)-5-methyl-5-vinyloxazolidine-2,4-dione |
| L | Ethyl 3-(3,5-dichlorophenyl)-5-methyl-2,4-dioxooxazolidine-5-carboxylate structure | Ethyl (RS)—3-(3',5'-dichlorophenyl)-5-methyl-2,4-dioxooxazolidine-5-carboxylate |

Besides, the anilides (I) may be also used ub admixture with other fungicides, herbicides, insecticides, miticides, fertilizers, etc.

When the anilides (I) are used as fungicides, they may be applied in such amounts as 2 to 100 grams per 10 ares. However, this amount may vary depending upon formulation forms, application times, application methods, application sites, diseases, crops and so on, and therefore, they are not limited to particalar amounts.

Some practical embodiments of the fungicidal composition according to the invention are shown in the following Examples wherein % and part(s) are by weight.

FORMULATION EXAMPLE 1

Two parts of Compound No. 9, 88 parts of clay and 10 parts of talc are thoroughly pulverized and mixed together to obtain a dust formulation containing 2% of the active ingredient.

FORMULATION EXAMPLE 2

Fifty parts of Compound No. 25, 25 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder formulation containing 50% of the active ingredient.

FORMULATION EXAMPLE 3

Twenty-five parts of Compound No. 37, 50 parts of Compound I, 18 parts of diatomaceous earth, 3.5 parts of calcium alkylbenzenesulfonate as a wetting agent and 3.5 parts of calcium ligninsulfonate as a dispersing agent are mixed while being powdered to obtain a wettable powder formulation containing 75% of the active ingredient.

FORMULATION EXAMPLE 4

Twenty parts of Compound No. 44, 30 parts of Compound A, 40 parts of powdery sucrose, 5 parts of white carbon, 3 parts of sodium laurylsulfate as a wetting agent and 2 parts of clacium ligninsulfonate as a dispersing agent are mixed while being powdered to obtain a wettable powder formulation containing 50% of the active ingredient.

Typical test data indicating the excellent fungicidal activity of the anilides (I) are shown below. The compounds used for comparison are as follows:

| Compound | Remarks |
| --- | --- |
| Benomyl 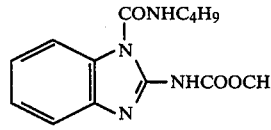 | Commercially available fungicide |
| Thiophanate-methyl 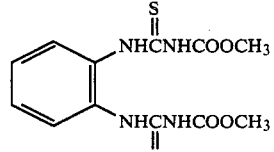 | Commercially available fungicide |
| Carbendazim 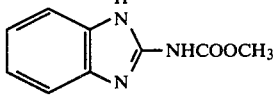 | Commercially available fungicide |
| Thiabendazole 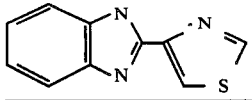 | Commercially available fungicide |

EXPERIMENT 1

Protective Activity Test on Powdery Mildew of Cucumber (*Sphaerotheca fuliginea*)

A flower pot of 90 ml volume was filed with sandy soil, and seeds of cucumber (var: Sagami-hanjiro) were sowed therein. Cultivation was carried out in a greenhouse for 8 days. Onto the resulting seedlings having cotyledons, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. Thedegree of damage was determined in the following manner, and the results are shown in Table 4.

The leaves examined were measured for a percentage of infected area and classified into the corresponding disease indices, 0, 0.5, 1, 3, 4:

| Disease index | Percentage of infected area |
| --- | --- |
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation:

$$\text{Disease severity (\%)} = \frac{\Sigma\{(\text{Disease index}) \times (\text{Number of leaves})\}}{4 \times (\text{Total number of leaves examined})} \times 100$$

The prevention value was calculated according to the following equation:

$$\text{Prevention value (\%)} = 100 - \frac{(\text{Disease severity in treated plot})}{(\text{Disease severity in untreated plot})} \times 100$$

TABLE 4

| Compound No. | Concentration of active ingredient (ppm) | Prevention value when inoculated with drug-resistant strain (%) | Prevention value when inoculated with drug-sensitive strain (%) |
| --- | --- | --- | --- |
| 9 | 200 | 97 | 0 |
| 12 | 200 | 97 | 0 |
| 13 | 200 | 100 | 0 |
| 19 | 200 | 100 | 0 |
| 25 | 200 | 100 | 0 |

TABLE 4-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| 26 | 200 | 100 | 0 |
| 42 | 200 | 97 | 0 |
| 44 | 200 | 100 | 0 |
| Benomyl | 200 | 0 | 100 |
| Thiophanate-methyl | 200 | 0 | 100 |
| Carbendazim | 200 | 0 | 100 |

As understood from the results shown in Table 4, the anilides (I) of the invention exhibit an excellent preventive effect on the drug-resistant strain but do not exhibit any preventive effect on the tested drug-sensitive strain. To the contrary, commercially available known fungicides such as Benomyl, Thiophanate-methyl and Carbendazim exhibit a notable controlling effect on the drug-sensitive strain but not on the drug-resistant strain. Other tested compounds structurally similar to the anilides (I) do not exhibit any fungicidal activity on the drug-sensitive strain and the drug-resistant strain.

EXPERIMENT 2

Preventive Effect on Cercospora Leaf Spot of Sugarbeet (*Cercospora beticola*)

A flower pot of 90 ml volume was filled with sandy soil, and seeds of sugarbeet (var: Detroit dark red) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chlorid sheet to make a condition of high humidity, and cultivation was continued in the greenhouse for 10 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
| --- | --- | --- | --- |
| 13 | 200 | 97 | 0 |
| 18 | 200 | 97 | 0 |
| 19 | 200 | 100 | 0 |
| 25 | 200 | 100 | 0 |
| 44 | 200 | 100 | 0 |
| Benomyl | 200 | 0 | 100 |
| Thiophanate-methyl | 200 | 0 | 100 |
| Carbendazim | 200 | 0 | 100 |

As understood from the results shown in Table 5, the anilide (I) of the invention exhibit an excellent preventive effect on the drug-resistant strain but do not exhibit any preventive effect on the tested drug-sensitive strain. To the contrary, commecially available known fungicides such as Benomyl, Thiophanate-methyl and Carbendazim exhibit a notable controlling effect on the drug-sensitive strain but not on the drug-resistant strain. Other tested compounds structurally similar to the anilides (I) do not exhibit any fungicidal activity on the drug-sensitive strain and the drug-resistant strain.

EXPERIMENT 3

Preventive Effect on Scab of Pear (*Venturia nashicola*)

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
| --- | --- | --- | --- |
| 12 | 200 | 94 | 0 |
| 19 | 200 | 100 | 0 |
| 36 | 200 | 100 | 0 |
| 42 | 200 | 97 | 0 |
| 44 | 200 | 100 | 0 |
| Benomyl | 200 | 0 | 100 |
| Thiophanate-methyl | 200 | 0 | 100 |

As understood from the results shown in Table 6, the anilides (I) of the invention exhibit an excellent preventive effect on the drug-resistant strain but do not exhibit any preventive effect on the tested drug-sensitive strain. To the contrary, commercially available known fungicidee such as Benomyl and Thioophanate-methyl exhibit a notable controlling effect on the drug-sensitive strain but not on the drug-resistant strain.

EXPERIMENT 4

Preventive Effect on Gray Mold of Cucumber (*Botrytis cinerea*)

Plastic pots of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Botrytis cinerea* by putting them on the leaf surfaces. After the plants were infected by incubating under high humidity at 20° C. for 3 days, the rates of disease severity were observed. The degree of damage was determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
|---|---|---|---|
| 1 | 200 | 88 | 0 |
| 2 | 200 | 88 | 0 |
| 3 | 500 | 88 | 0 |
| 4 | 200 | 94 | 0 |
| 5 | 200 | 88 | 0 |
| 6 | 200 | 96 | 0 |
| 7 | 200 | 94 | 0 |
| 8 | 200 | 100 | 0 |
| 9 | 200 | 100 | 0 |
| 10 | 200 | 96 | 0 |
| 11 | 200 | 88 | 0 |
| 12 | 200 | 100 | 0 |
| 13 | 200 | 100 | 0 |
| 14 | 200 | 88 | 0 |
| 15 | 200 | 100 | 0 |
| 16 | 200 | 92 | 0 |
| 17 | 200 | 100 | 0 |
| 18 | 200 | 100 | 0 |
| 19 | 200 | 100 | 0 |
| 20 | 200 | 100 | 0 |
| 21 | 200 | 100 | 0 |
| 22 | 200 | 100 | 0 |
| 23 | 200 | 100 | 0 |
| 24 | 200 | 98 | 0 |
| 25 | 200 | 100 | 0 |
| 26 | 200 | 100 | 0 |
| 27 | 200 | 98 | 0 |
| 28 | 200 | 94 | 0 |
| 29 | 200 | 100 | 0 |
| 30 | 200 | 100 | 0 |
| 31 | 200 | 100 | 0 |
| 32 | 200 | 100 | 0 |
| 33 | 200 | 88 | 0 |
| 34 | 200 | 88 | 0 |
| 35 | 200 | 94 | 0 |
| 36 | 200 | 97 | 0 |
| 37 | 200 | 100 | 0 |
| 38 | 200 | 100 | 0 |
| 39 | 200 | 92 | 0 |
| 40 | 200 | 100 | 0 |
| 41 | 200 | 88 | 0 |
| 42 | 200 | 100 | 0 |
| 43 | 200 | 97 | 0 |
| 44 | 200 | 100 | 0 |
| 45 | 200 | 92 | 0 |
| 46 | 200 | 100 | 0 |
| 47 | 200 | 94 | 0 |
| 48 | 200 | 100 | 0 |
| 49 | 200 | 100 | 0 |
| 50 | 200 | 88 | 0 |
| 51 | 200 | 100 | 0 |
| 52 | 200 | 88 | 0 |
| 53 | 200 | 94 | 0 |
| 54 | 200 | 100 | 0 |
| 55 | 200 | 100 | 0 |
| 56 | 200 | 100 | 0 |
| 57 | 200 | 94 | 0 |
| 58 | 200 | 98 | 0 |
| 59 | 200 | 98 | 0 |
| 60 | 200 | 88 | 0 |
| 61 | 200 | 88 | 0 |
| 62 | 200 | 94 | 0 |
| 63 | 200 | 100 | 0 |
| 64 | 200 | 100 | 0 |
| 65 | 200 | 100 | 0 |
| 66 | 500 | 94 | 0 |
| 67 | 500 | 88 | 0 |
| 68 | 200 | 100 | 0 |
| 69 | 200 | 100 | 0 |
| 70 | 500 | 96 | 0 |
| 71 | 200 | 98 | 0 |
| 72 | 200 | 100 | 0 |
| 73 | 200 | 100 | 0 |
| 74 | 200 | 100 | 0 |
| 75 | 200 | 92 | 0 |
| 76 | 200 | 100 | 0 |
| 77 | 200 | 100 | 0 |
| 78 | 200 | 100 | 0 |
| 79 | 200 | 100 | 0 |
| 80 | 500 | 98 | 0 |
| 81 | 500 | 88 | 0 |
| 82 | 500 | 92 | 0 |
| 83 | 200 | 100 | 0 |
| 84 | 500 | 94 | 0 |
| 85 | 500 | 92 | 0 |
| 86 | 200 | 100 | 0 |
| 87 | 200 | 98 | 0 |
| 88 | 200 | 94 | 0 |
| 89 | 200 | 100 | 0 |
| 90 | 200 | 98 | 0 |
| 91 | 200 | 100 | 0 |
| Benomyl | 200 | 0 | 100 |
| Thiophanate-methyl | 200 | 0 | 100 |

As understood from the results shown in Table 7, the anilides (I) of the invention exhibit an excellent preventive effect on the drug-resistant stain but do not exhibit any preventive effect onto the tested drug-sensitive strain. To the contrary, commercially available known fungicides such as Benomyl and Thiophanate-methyl exhibit a notable controlling effect on the drug-sensitive strain but not on the drug-resistant strain.

EXPERIMENT 5

Preventive Effect on Powdery Mildew of Cucumber (*Sphaerotheca fuliginea*)

A plastic pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Sphaerotheca fuliginea* by spraying and further cultivated in the greenhouse. Ten days thereafter, the infectious state of the plants was observed. The degree of damage was determined in the same manner as in Experiment 1, and the results are shown in Table 8.

TABLE 8

| Compound No. | Concentration of active ingredient (ppm) | Prevention value (%) |
|---|---|---|
| 19 | 100 | 34 |
| 19 | 20 | 0 |
| 25 | 100 | 42 |
| 25 | 20 | 0 |
| 37 | 100 | 42 |
| 37 | 20 | 0 |
| 42 | 100 | 44 |
| 42 | 20 | 0 |
| 44 | 100 | 45 |
| 44 | 20 | 0 |
| A | 100 | 44 |
| A | 20 | 19 |
| B | 500 | 45 |
| B | 100 | 10 |
| C | 100 | 44 |
| C | 20 | 12 |
| D | 500 | 36 |
| D | 100 | 0 |

TABLE 8-continued

| Compound No. | Concentration of active ingredient (ppm) | Prevention value (%) |
| --- | --- | --- |
| E | 100 | 42 |
| E | 20 | 10 |
| F | 100 | 45 |
| F | 20 | 8 |
| G | 100 | 42 |
| G | 20 | 8 |
| H | 100 | 40 |
| H | 20 | 5 |
| 19 + A | 20 + 20 | 100 |
| 19 + B | 20 + 20 | 100 |
| 19 + E | 20 + 20 | 100 |
| 19 + G | 20 + 20 | 100 |
| 25 + C | 20 + 20 | 100 |
| 25 + D | 20 + 20 | 100 |
| 25 + F | 20 + 20 | 100 |
| 25 + H | 20 + 20 | 100 |
| 37 + A | 20 + 20 | 100 |
| 37 + D | 20 + 20 | 100 |
| 37 + E | 20 + 20 | 100 |
| 37 + G | 20 + 20 | 100 |
| 42 + A | 20 + 20 | 100 |
| 42 + B | 20 + 20 | 100 |
| 42 + E | 20 + 20 | 100 |
| 42 + G | 20 + 20 | 100 |
| 44 + B | 20 + 20 | 100 |
| 44 + C | 20 + 20 | 100 |
| 44 + E | 20 + 20 | 100 |
| 44 + H | 20 + 20 | 100 |

As understood from the results shown in Table 8, the combined use of the anilides (I) of the invention with benzimidazole thiophanate fungicides and/or cyclic imide fungicides exhibit a much more excellent preventive effect than their sole use.

EXPERIMENT 6

Preventive Effect on Gray Mold of Tomato (*Botrytis cinerea*)

A plastic pot of 90 ml volume was filled with sandy soil, and seeds of tomato (var: Fukuji No. 2) were sowed therein. Cultivation was carried out in a greenhouse for 4 weeks. Onto the resulting seedlings at the 4-leaf stage, the test compound(s) formulated in emulsifiable concentrated or wettable powder and diluted with water were sprayed at a rate of 10 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damge was determined in the same manner as in Experiment 1, and the results are shown in Table 9.

TABLE 9

| Compound No. | Concentration of active ingredient (ppm) | Prevention value (%) |
| --- | --- | --- |
| 18 | 100 | 28 |
| 18 | 20 | 0 |
| 25 | 100 | 34 |
| 25 | 20 | 0 |
| 44 | 100 | 42 |
| 44 | 20 | 0 |
| I | 100 | 48 |
| I | 20 | 22 |
| J | 500 | 44 |
| J | 100 | 18 |
| K | 100 | 42 |
| K | 20 | 12 |
| L | 500 | 45 |
| L | 100 | 10 |
| 18 + I | 20 + 50 | 100 |
| 18 + J | 20 + 50 | 100 |

TABLE 9-continued

| Compound No. | Concentration of active ingredient (ppm) | Prevention value (%) |
| --- | --- | --- |
| 25 + I | 20 + 50 | 100 |
| 25 + K | 20 + 50 | 100 |
| 44 + I | 20 + 50 | 100 |
| 44 + J | 20 + 50 | 100 |
| 44 + K | 20 + 50 | 100 |
| 44 + L | 20 + 50 | 100 |

As understood from the results shown in Table 9, the combined use of the anilides (I) of the invention with benzimidazole thiophanate fungicides and/or cyclic imide fungicides exhibit a much more excellent preventive effect than their sole use.

What is claimed is:

1. A fungicidal composition which comprises as an active ingredient a fungicidally effective amount of an anilide of the formula:

$$\text{Z} \underset{\text{Y}}{\overset{\text{X}}{\diagup\!\!\!\diagdown}} \text{NH} - \overset{\text{O}}{\underset{\|}{\text{C}}} - \text{R}^1$$

wherin X is halogen; Z and Y are a lower alkoxy group; and $R_1$ is a $C_1$–$C_7$ alkyl group or a $C_2$–$C_6$ alkenyl group; and an inert carrier.

2. The fungicidal composition as recited in claim 1, wherein the anilide is represented by the formula:

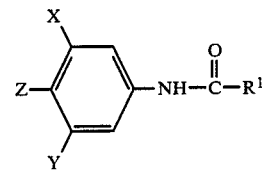

3. The fungicidal composition as recited in claim 1, wherein the anilide is represented by the formula:

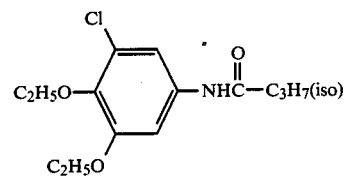

4. The fungicidal composition as recited in claim 1, wherein the anilide is represented by the formula:

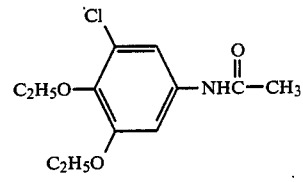

5. The fungicidal composition as recited in claim 1, wherein the anilide is represented by the formula:

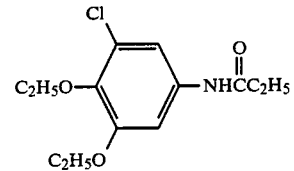

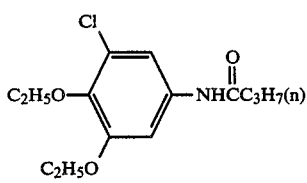

6. The fungicidal composition as recited in claim 1, wherein the anilide is represented by the formula:

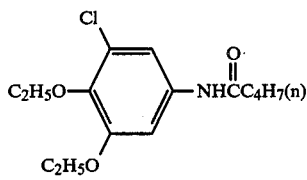

7. The fungicidal composition as recited in claim 1, wherein the anilide is represented by the formula:

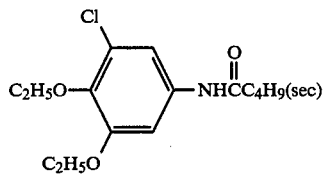

8. The fungicidal composition as recited in claim 1, wherein the anilide is represented by the formula:

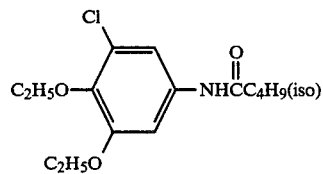

9. The fungicidal composition as recited in claim 1, wherein the anilide is represented by the formula:

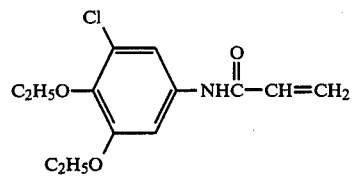

10. The fungicidal composition as recited in claim 1, wherein the anilide is represented by the formula:

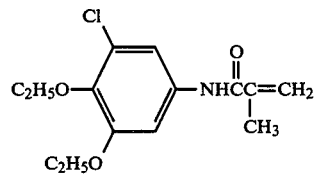

11. The fungicidal composition as recited in claim 1, wherein the anilide is represented by the formula:

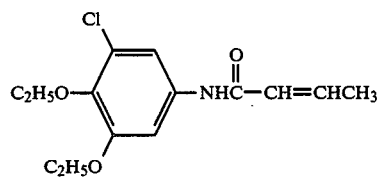

12. A method for controlling plant pathogenic fungi which comprises applying a fungicidally effective amount of at least one of the anilides of the formula:

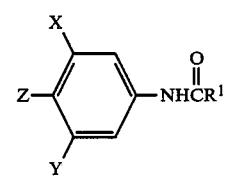

wherein X, Y, Z and $R_1$ are each as defined in claim 1, to plant pathogenic fungi.

13. The method according to claim 12, wherein the plant pathogenic fungi is the drug-resistant strain.

* * * * *